(12) United States Patent
Meyer

(10) Patent No.: US 8,091,891 B2
(45) Date of Patent: Jan. 10, 2012

(54) DEVICE FOR TREATING SHEET-LIKE SUBSTRATES WITH LIGHT

(76) Inventor: Gerhard Meyer, Neusaess (DE)

(*) Notice: Subject to any disclaimer, the term of this patent is extended or adjusted under 35 U.S.C. 154(b) by 0 days.

(21) Appl. No.: 12/833,914

(22) Filed: Jul. 9, 2010

(65) Prior Publication Data

US 2011/0013170 A1   Jan. 20, 2011

(30) Foreign Application Priority Data

Jul. 14, 2009   (DE) .......................... 10 2009 032 966

(51) Int. Cl.
 *B65H 5/02* (2006.01)
(52) U.S. Cl. ........................................ 271/276; 271/196
(58) Field of Classification Search .................. 271/276, 271/196, 197; 358/496, 498
See application file for complete search history.

(56) References Cited

U.S. PATENT DOCUMENTS

| 4,447,817 A | * | 5/1984 | Naramore ...................... 347/104 |
| 5,810,350 A | * | 9/1998 | Pollich .......................... 271/276 |
| 7,293,770 B2 | * | 11/2007 | Edinger ........................ 271/276 |
| 2004/0164482 A1 | * | 8/2004 | Edinger ........................ 271/197 |

FOREIGN PATENT DOCUMENTS

JP   62185652 A   *   8/1987

* cited by examiner

*Primary Examiner* — David H Bollinger
(74) *Attorney, Agent, or Firm* — Edwin D. Schindler

(57) ABSTRACT

A device for treating sheet-like substrates with light is made for a suction table, which includes a circulating suction strip for transporting the sheet-like substrates, which suction strip forms a descending loop relative to its table-parallel transport level. The loop has a descending branch and, adjacent to the latter, an ascending branch. There is a gap for the passage of light between the descending branch and the ascending branch of the suction strip, which is bridged by a stationary bridging member which at least partially allows light to pass through it and whose surface is disposed at a level slightly recessed relative to the parallel transport level, so that a high degree of accuracy and trouble-free operation are ensured even at high transport speeds.

16 Claims, 2 Drawing Sheets

DEVICE FOR TREATING SHEET-LIKE SUBSTRATES WITH LIGHT

FIELD OF THE INVENTION

This invention relates to a device for treating sheet-like substrates with light, in particular for transmitted light checks of sheet-like substrates made of paper.

BACKGROUND OF THE INVENTION

To assure adequate quality in paper manufacturing and/or processing, optical checks are required, e.g., in the form of transillumination. On one side of the substrate provision is made for an illumination device, while on the other side thereof provision is made for a camera. To achieve a maximum resolution of the photos the substrate should be completely level while being moved past the camera at a fixed distance therefrom. This is unproblematic when strip-like material is processed. In processing sheet-like substrates having a front and rear edge of the sheet, however, this is difficult. In this context it has to be ensured that the transmitted light checks require a gap in the region of the transport level, allowing a light beam to pass through, and that for this reason the substrate is not guided as it passes across the gap. As a consequence of the absence of such guidance, the substrates passing across the gap, in particular at high transport speeds, may be warped or distorted in the region of the said gap, which would result in imprecise photos, malfunctions or stoppages.

On these premises it is therefore the object of the present invention to improve a device as described initially above in such a way that a high transport speed of the sheet-like substrates is permitted, while a high degree of treatment accuracy and trouble-free operation is ensured.

SUMMARY OF THE INVENTION

This object is achieved by the following proposal:

A device for treating sheet-like substrates with light, in particular for transmitted light checks of sheet-like substrates made of paper, comprising a suction table which is provided with a circulating suction strip for transporting the sheet-like substrates, which suction strip forms a descending loop relative to its table-parallel transport level, such loop comprising a descending branch and, adjacent to the latter, an ascending branch, with a gap for the passage of light between the descending and the ascending branch of the suction strip being bridged by a stationary bridging member which at least partially allows light to pass through it and whose surface is disposed at a level slightly recessed relative to the parallel transport level.

With these measures the above object is achieved in a most simple and low-cost manner. The loop formed by the suction strip results in the provision of a gap which is required for the passage of light. As a consequence of the recessed surface of the stationary bridge member bridging the said gap relative to the upper transport level of the suction strip, a small clearance is formed between the front edge of the sheet and the surface of the bridge member as the front edge of the sheet enters the gap area, which prevents the front edge of the sheet from contacting any stationary components, thus eliminating the danger of it being upset. In the said gap between the entering substrate and the surface of the bridging member a certain partial vacuum is immediately caused assuring firm contact of the sheet with the bridge member, whereby a defined distance from the camera is ensured and a high degree of resolution is achieved. At the same time, the air flowing off forms an air cushion reducing friction, so that even in the case of relatively thin substrates the degree of their stiffness is sufficient to allow them to be moved across the comparatively narrow gap area without being creased. The measures according to the invention thus ensure a high degree of accuracy as well as trouble-free operation.

Advantageous embodiments and expedient developments of the main-claim measures will be evident from the sub-claims.

Thus the amount of recess of the surface of the bridging member relative to the transport level of the suction strip should expediently be somewhat greater than the thickness of the sheet-like substrates, with experience having shown that an amount of between 0.5 and 0.8 mm can be expected to yield particular good results.

Advantageously, adjusting means for lowering the surface of the bridging member may be provided which permit the adjustment of its level to suit the conditions in each individual case.

The bridge member used for transmitted light checks may possess a transparent plate with a smooth surface, preferably in the form of a glass plate. This ensures good contact of the substrate with the plate.

A further advantageous embodiment of the measures as described above may consist in the suction strip being designed as a spiral screen mesh strip. Such a strip affords the advantage of possessing good air permeability with a cross-sectional proportion of approximately 50 per cent, and at the same time permits compliance with close tolerance limits with respect to the relevant measurements.

Advantageously, the suction table may comprise an evacuable box whose at least partially open upper side is passed over by the suction strip. It is thus ensured that the deflection of the suction strip for the formation of the loop is located entirely in the suction area, so that the suction strip seizes the front edge of the sheet immediately after the latter has passed the exposure gap and/or securely holds a rear end of the sheet until it has reached the exposure gap.

Expediently, the transparent plate associated with the bridge member may be held by a mounting frame, which ensures a high degree of stability and simultaneously facilitates the connection with control elements.

A further advantageous measure may consist in the bridge member possessing bevelled lateral edges and thus being movable into contact with the adjacent suction strip deflection areas. For this reason, it can be prevented that even in the case of comparatively large deflection radii gaps are formed that may suck up inleaked air. It is thus possible in an advantageous manner to provide deflection rollers for the deflection of the suction strip, which enable smooth operation.

Further advantageous embodiments and expedient developments of the main-claim measures will be evident from the remaining sub-claims and from the description of an example given below in conjunction with the accompanying drawings.

BRIEF DESCRIPTION OF THE DRAWING FIGURES

DETAILED DESCRIPTION OF THE DRAWING FIGURES AND PREFERRED EMBODIMENTS

The main field of application of the invention is in the realm of transmitted light checks of sheet-like substrates, in particular for the purpose of recognizing water marks in security-relevant sheets, e.g., banknotes, or laser treatment for example in the form of a perforation of such sheets.

Figure 1:
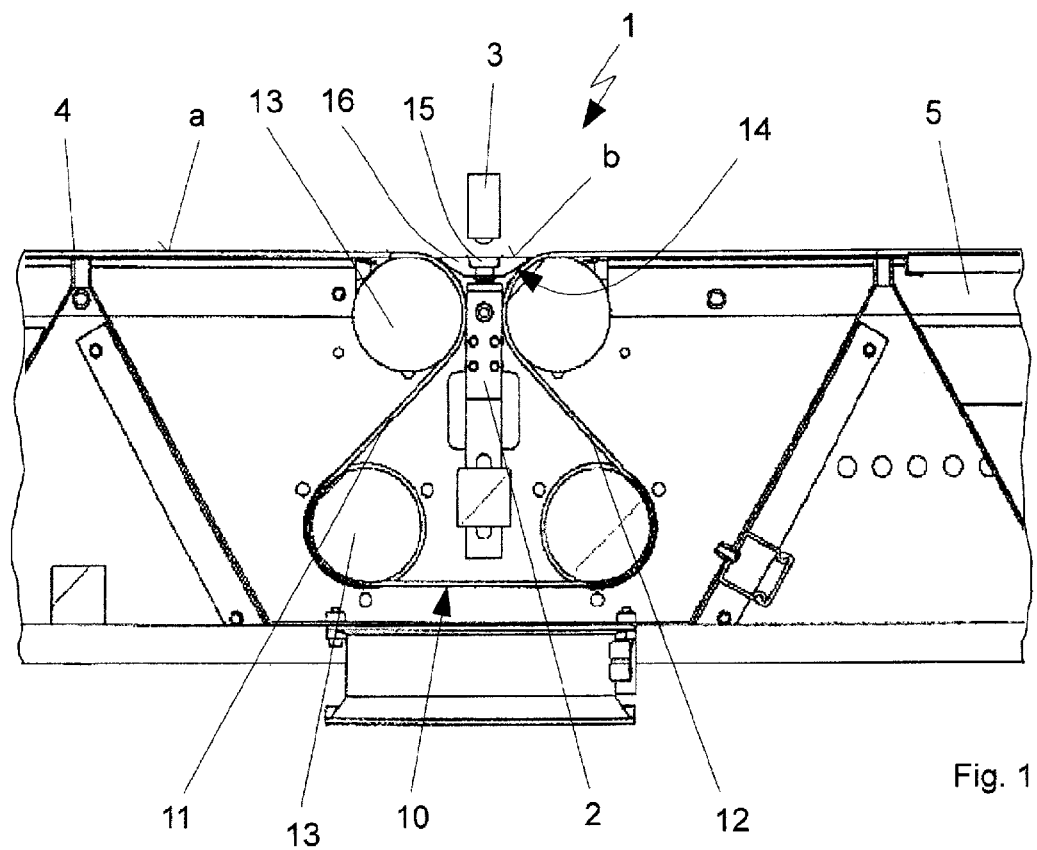
FIG. 1 is a part-sectional view of a transmitted light check device.

Underlying FIG. 1 is a device for transmitted light checks of sheet-like substrates. The device possesses a checking station 1 comprising an illumination device 2 arranged below the transport level of the sheet-like substrates, and a camera 3 arranged above the transport level. Likewise conceivable would be a reverse arrangement with the camera arranged below and the illumination device arranged above. The illumination device 2 expediently possesses one or several LEDs which may form high luminosity illumination units. The camera 3 is expediently designed as a line camera which, at a certain raster set to correspond to the desired resolution, takes photographs of a line sector spanning the entire width of the substrate. The data corresponding to such photographs will then be transmitted by the camera 3 to evaluation electronics not shown here in detail, which assembles the said data to form a complete picture.

Figure 2:
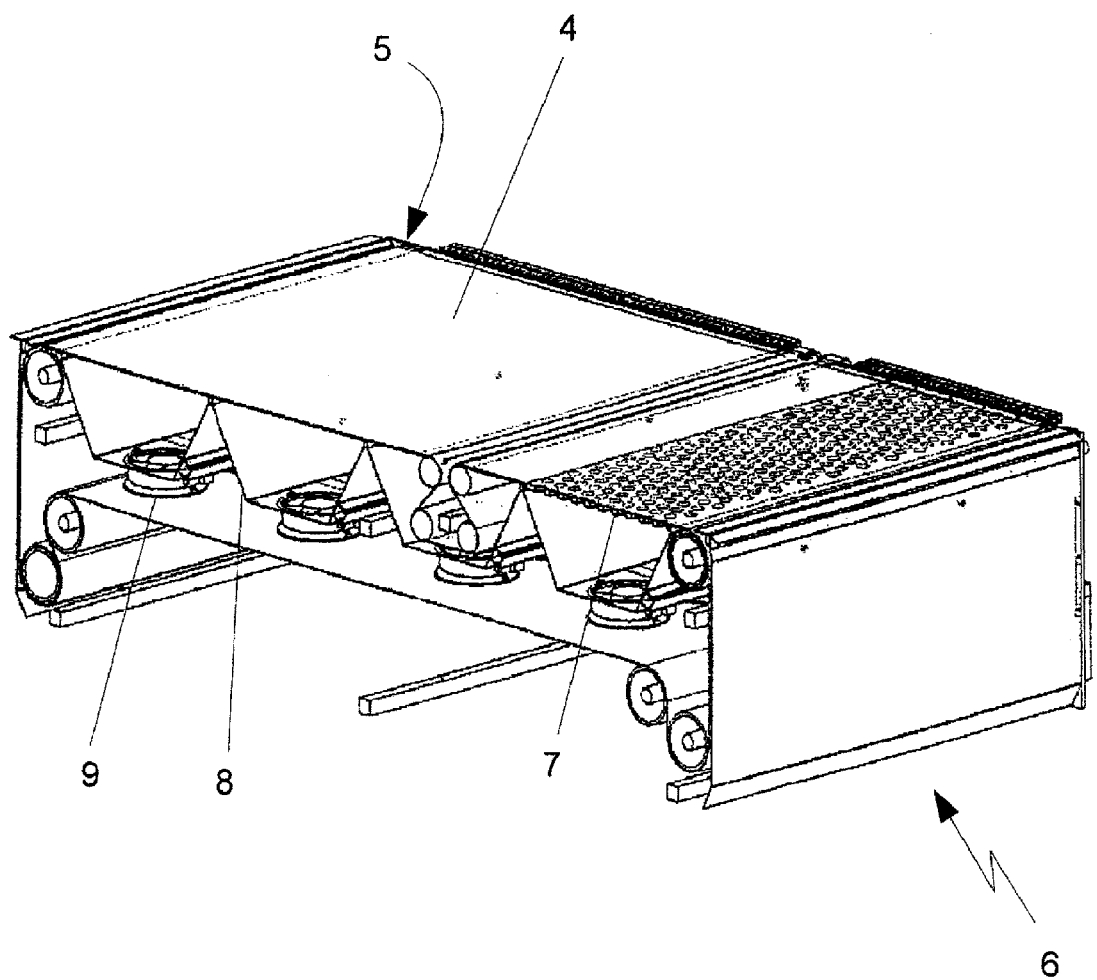
FIG. 2 is a schematic general view of the suction table underlying FIG. 1.

For transporting the sheet-like substrates provision is made for a transport device. The latter comprises a circulating, drivable suction strip 4 which is received by an associated suction table 5. The latter, as can best be seen from FIG. 2, forms the upper side of an evacuable box 6 whose at least partially open or perforated upper side is passed over by the suction strip 4. In order to support the suction strip 4 the suction table may at least partially be formed by perforated plates 7, as is indicated in FIG. 2 on the right. The box 6 is expediently subdivided into sections which are formed by inserts 8 open towards the top and having a chute-like cross section, which sections are partially evacuated by associated air suction fans 9.

Expediently, the suction strip 4 is designed as a spiral screen mesh strip. It can be manufactured to very close tolerances and expediently possesses an air permeability of approximately up to 50 percent. Such a spiral screen mesh strip consists of a thread which is wound spirally and transverse to the moving direction of the strip around two more threads, so-called wefts, which are arranged at a certain mutual distance from one another. When one lateral edge of the strip is reached the thread will be laid around the next weft in the direction of strip movement, and is further on wound transverse to the running direction until the opposite lateral edge has been reached. In this manner a highly uniform structure of the strip and good air permeability are achieved, so that the suction flow generated by the air suction fans 9 can effectively pass through the suction strip 4.

To prevent the camera 3 from depicting the strip structure the suction strip 4 in the area of the check station 1 extends in the form of a loop 10 which relative to the effective transport level a of the suction strip 4 runs in a downward direction and circumvents the check station, here the illumination device 2, which is arranged below the transport level "a", such loop 10 comprising a descending branch 11 and, adjacent to it, an ascending branch 12. In order to deflect the suction strip 4 for forming the loop 10, provision is made for four deflection units, in this case in the form of deflection rollers 13, around part of which the suction strip 4 moves and which are arranged at the corners of a regular trapezium having a short upper side. In this manner, between the upper deflection rollers and hence between the upper ends of the descending branch 11 and the ascending branch 12, respectively, of the suction strip 4 a comparatively small gap is formed whose width is sufficiently large to allow the required light beam to pass through it. Experience has shown that in using high luminosity LEDs for forming the illumination device 2 just a few centimetres will be sufficient to obtain an intensive and uniform illumination strip which is required for the transmitted light checks. It is likewise conceivable to use stationary elements, such as deflection rods or knife edges instead of rotatable deflection rollers 13. The deflection rollers, however, ensure a gentle and low-friction operation.

The above-mentioned gap between the upper ends of the descending branch 11 and the ascending branch 12, respectively, of the suction strip 4 is bridged by a stationary bridging member 14 having a design which is at least partially light-permeable. In the example shown, the bridge member 14 possesses a plate 15 which is made of a transparent material, preferably of glass, and inserted in a sturdy mounting frame 16. In the example relating to transmitted light checks the glass plate 15 and the mounting frame 16 possess a smooth surface. In a device for laser treating the sheet-like substrates the bridge member 14 may comprise a plate provided with perforations for the laser beams and possess spacing cams projecting in an upward direction.

The regions of the suction strip 4 flanking the check station 1 and arranged upstream or downstream of the loop 10 define the parallel, in this case horizontal, transportation level "a". The surface "b" of the bridge member 14 is slightly recessed relative to the transport level "a". This recess corresponds at least to the thickness, but should preferably be slightly greater than the thickness of the sheet-like substrates to be processed, so that the front edge of a sheet-like substrate entering the check station 1 cannot contact any stationary parts. At the same time, between the front area of the sheet of a substrate and the surface "b" of the bridge member 14 a small gap is formed from which air is exhausted, thus causing a partial vacuum which pulls the substrate against the surface "b", which in turn results in a firm and level support thereof at a fixed distance from the camera 3.

The front edge of the sheet entering the check station 1 is practically without guidance. The substrate is thus only moved forward by that portion of the suction strip 4 which is arranged ahead of the check station. As soon as the front edge of the sheet has passed the check station 1 and reached the portion of the suction strip 4 arranged downstream thereof, the suction strip 4 continues to pull the substrate, thus restoring guidance of the front edge of the sheet. Owing to the good surface quality of the bridge member 14 and the plate 15, respectively, and due to the air cushion formed by the air being exhausted, the substrate's degree of stiffness is sufficient to move the front edge of the sheet reliably through the check station 1. As a result of the said partial vacuum, the rear edge of the sheet released by the suction strip 4 and entering the check station 1 will thus be kept in firm contact with the bridge member 14.

Figure 3:
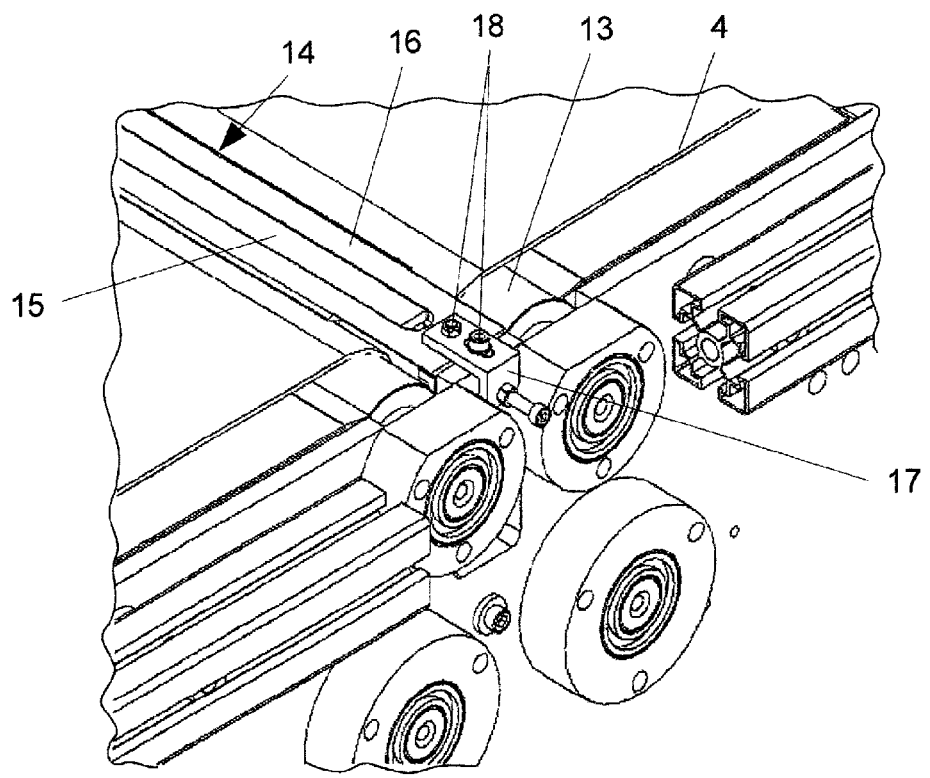
FIG. 3 is a perspective partial lateral view of the arrangement according to FIG. 2 of the suction strip deflection area.

A recess of 0.5 to 0.8 mm of the surface "b" relative to the transport level is expected to yield good results. Expediently, the bridge member 16 may be arranged in such a manner that the amount of such recess can be adjusted to suit conditions in each individual case. According to FIG. 3, the ends of the support frame 16 are adjustably attached to mounting brackets 17 which in turn are mountable on the side of the table and associated with adjusting and tensioning screws 18. The front and rear lateral edges of the bridge member 14 are bevelled in the direction of strip movement to suit the configuration of the adjacent deflection rollers 13, so that the bridge member 13 is movable into close contact with, or can even be more or less pushed against, the regions of the suction strip 4 which move into the loop 10 or out of it, so that gaps therebetween can largely be avoided.

What is claimed is:

1. An apparatus for treating sheet substrates with light, comprising a suction table having a circulating suction strip for transporting the sheet substrates, the circulating suction strip forms a descending loop relative to, and beneath, a suction table-parallel transport level of the circulating suction strip, said descending loop comprising a descending branch and, adjacent to the descending branch, an ascending branch, with a gap for the passage of light between the descending branch and the ascending branch of the circulating suction strip being bridged by a stationary bridging member which at least partially allows light to pass through it and whose surface is disposed at level slightly recessed relative to the suction table-parallel transport level.

2. The apparatus for treating sheet substrates with light according to claim 1, wherein the recess of the surface of the stationary bridging member relative to the suction table-parallel transport level of the circulating suction strip corresponds at least to the thickness of the sheet substrates.

3. The apparatus for treating sheet substrates with light according to claim 2, wherein the recess of the surface of the stationary bridging member relative to the suction-table parallel transport level of the circulating suction strip is in the region of between 0.5 and 0.8 mm.

4. The apparatus for treating sheet substrates with light according to claim 1, wherein the recess of the surface of the stationary bridging member relative to the suction-table parallel transport level of the circulating suction strip is adjustable.

5. The apparatus for treating sheet substrates with light according to claim 1, wherein the stationary bridging member includes a transparent glass plate having a smooth surface.

6. The apparatus for treating sheet substrates with light according to claim 5, wherein the transparent glass plate of the stationary bridge member is received by a mounting frame.

7. The apparatus for treating sheet substrates with light according to claim 6, wherein the mounting frame has lateral ends that received by mounting brackets which are adjustably mountable on the side of the suction table.

8. The apparatus for treating sheet substrates with light according to claim 5, wherein on a first side of the transparent glass plate of the stationary bridge member provision is made for an illumination device, while on a second side of the transparent glass plate provision is made for a camera.

9. The apparatus for treating sheet substrates with light according to claim 8, wherein the illumination device contains at least one LED.

10. The apparatus for treating sheet substrates with light according to claim 8, whereby the camera is a line-camera spanning a table width.

11. The apparatus for treating sheet substrates with light according to claim 1, wherein the stationary bridging member for a laser treatment is a perforated plate with spacing cams projecting in an upward direction.

12. The apparatus for treating sheet substrates with light according to claim 1, wherein the circulating suction strip is a spiral screen strip.

13. The apparatus for treating sheet substrates with light according to claim 1, wherein the suction table includes an evacuable box whose open upper side is passed over by the circulating suction strip.

14. The apparatus for treating sheet substrates with light according to claim 1, wherein the stationary bridging member has beveled lateral edges and is thus movable into contact with the adjacent deflection areas of the circulating suction strip.

15. The apparatus for treating sheet substrates with light according to claim 1, wherein four deflection rollers, at the corners of a regular trapezium, are associated with the circulating suction strip.

16. The apparatus for treating sheet substrates with light according to claim 1, wherein the stationary bridging member comprises a perforated plate having spacing cams projecting in an upward direction.

\* \* \* \* \*